United States Patent
Ryu et al.

(10) Patent No.: US 9,402,856 B2
(45) Date of Patent: Aug. 2, 2016

(54) PHARMACEUTICAL COMPOSITION FOR PREVENTING OR TREATING DIABETES CONTAINING TENC1 EXPRESSION OR ACTIVITY SUPPRESSOR

(71) Applicant: POSTECH ACADEMY-INDUSTRY FOUNDATION, Gyeongsangbuk-do (KR)

(72) Inventors: Sung Ho Ryu, Gyeongsangbuk-do (KR); A Ra Koh, Seoul (KR); Mi Nam Lee, Busan (KR); Hee Yoon Jeong, Gyeongsangbuk-do (KR); Yong Ryoul Yang, Gyeongsangbuk-do (KR); Pann Ghill Suh, Ulsan (KR)

(73) Assignee: Postech Academy-Industry Foundation (KR)

( * ) Notice: Subject to any disclaimer, the term of this patent is extended or adjusted under 35 U.S.C. 154(b) by 0 days.

(21) Appl. No.: 14/374,086

(22) PCT Filed: Jan. 14, 2013

(86) PCT No.: PCT/KR2013/000288
§ 371 (c)(1),
(2) Date: Jul. 23, 2014

(87) PCT Pub. No.: WO2013/115504
PCT Pub. Date: Aug. 8, 2013

(65) Prior Publication Data
US 2015/0038551 A1 Feb. 5, 2015

(30) Foreign Application Priority Data

Jan. 30, 2012 (KR) .................. 10-2012-0009249
Jan. 14, 2013 (KR) .................. 10-2013-0004101

(51) Int. Cl.
| | |
|---|---|
| *C12N 15/11* | (2006.01) |
| *A61K 31/713* | (2006.01) |
| *A61K 31/19* | (2006.01) |
| *A61K 31/7105* | (2006.01) |
| *C12Q 1/42* | (2006.01) |
| *C12N 15/113* | (2010.01) |
| *G01N 33/50* | (2006.01) |
| *A61K 38/00* | (2006.01) |

(52) U.S. Cl.
CPC .............. *A61K 31/713* (2013.01); *A61K 31/19* (2013.01); *A61K 31/7105* (2013.01); *C12N 15/1137* (2013.01); *C12Q 1/42* (2013.01); *G01N 33/5023* (2013.01); *A61K 38/00* (2013.01); *C12N 2310/14* (2013.01); *C12Y 301/03* (2013.01); *G01N 2333/916* (2013.01); *G01N 2500/04* (2013.01); *G01N 2500/10* (2013.01); *G01N 2800/042* (2013.01)

(58) Field of Classification Search
CPC . A61K 31/713; C12N 15/113; C12N 2310/14
See application file for complete search history.

(56) References Cited

FOREIGN PATENT DOCUMENTS

| | | |
|---|---|---|
| CN | 1988912 A | 6/2007 |
| CN | 101444518 | 6/2009 |
| CN | 101732323 A | 6/2010 |
| KR | 10-2010-0077160 | 7/2010 |
| KR | 10-2010-0135465 | 12/2010 |
| WO | WO 2011/146768 | 11/2011 |

OTHER PUBLICATIONS

Linda Paris, The Pew Charitable Trusts, From Lab Bench to Bedside: A backgrounder on Drug Development, Mar. 12, 2014, retrieved on Oct. 15, 2015, from http://www.pewtrusts.org/en/research-and-analysis/analysis/2014/03/12/from-lab-bench-to-bedside-a-backgrounder-on-drug-development, pp. 1-4.*
"1H, 15N and 13C chemical shift assignments of the SH2 domain of human tensing (TENC1)," Biomolecular NMR Assignments, Oct. 2011, vol. 5, Issue 2, pp. 211-214.
Hafizi et al., "Interaction of Axl receptor tyrosine kinase with C1-TEN, a novel C1 domain-containing protein with homology to tensin," 2002, Biochemical and Biophysical Research Communications, 299: 793-800.
Jung et al., "Tensin2 is a novel mediator in thrombopoietin (TPO)-induced cellular proliferation by promoting Akt signaling," 2011, Cell Cycle 10(11): 1838-1844.
Vadav et al., "Targeting Inflammatory Pathways by Triterpenoids for Prevention and Treatment of Cancer," *Toxins*, 2010, 2:2428-2466.
Hafizi et al., "C1-TEN is a negative regulator of the Akt/PKB signal transduction pathway and inhibits cell survival, proliferation and migration," *FASEB Journal*, 2005, 19:971-973.

* cited by examiner

*Primary Examiner* — Brian Whiteman
(74) *Attorney, Agent, or Firm* — Riverside Law LLP

(57) ABSTRACT

The present invention relates to a pharmaceutical composition for preventing or treating diabetes or a complication of diabetes, which includes a TENC1 (tensin like C1 domain-containing phosphatase) expression or activity suppressor, and, more specifically, relates to a pharmaceutical composition for preventing or treating diabetes or a complication of diabetes, which either suppresses the degradation of IRS-1 (insulin receptor substrate-1) or suppresses the phosphorylation of IRS-1 due to the PTPase activity of TENC1. The pharmaceutical composition according to the present invention, which is for preventing or treating diabetes or a complication of diabetes and comprises the TENC1 expression or activity suppressor as an active ingredient, can be expected to be widely usable in preventing and treating diabetes or a complication of diabetes since the pharmaceutical composition can effectively prevent the muscular dystrophy and reduction in sugar adsorption that occur due to reduction in IRS-1 by suppressing degradation of IRS-1 caused by TENC1.

7 Claims, 13 Drawing Sheets

FIG. 1
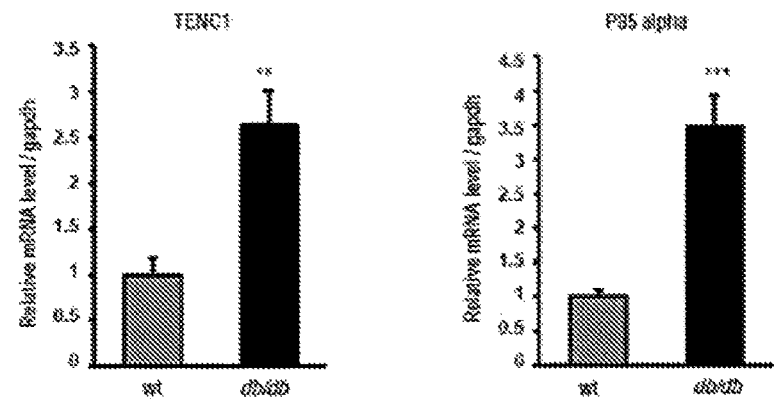
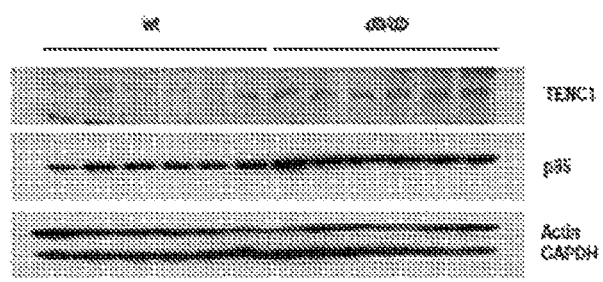
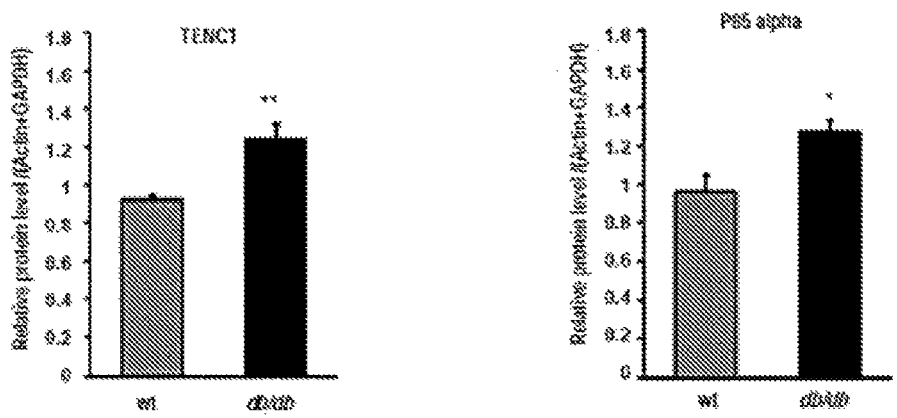

FIG. 3
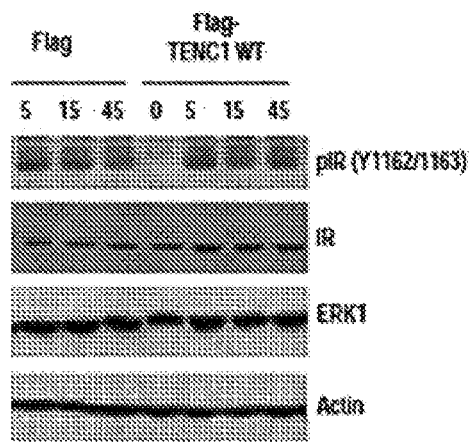
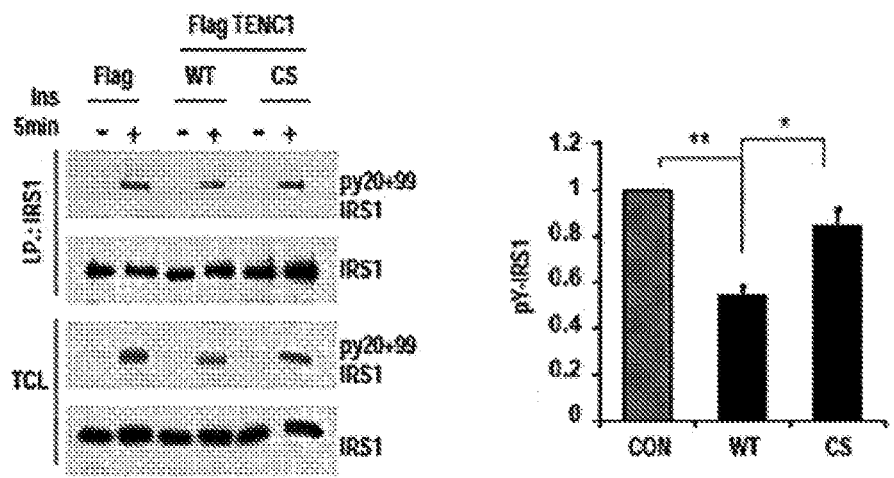

FIG. 16
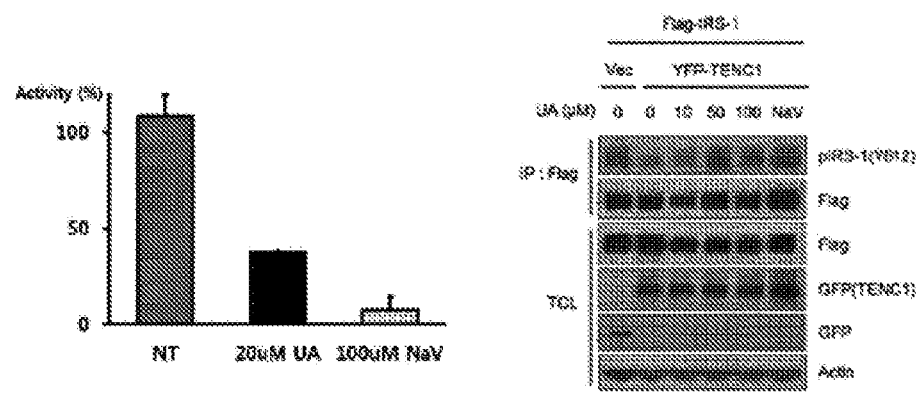
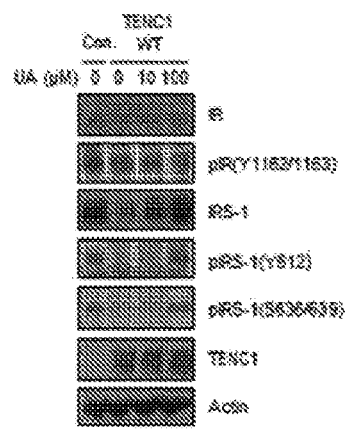

PHARMACEUTICAL COMPOSITION FOR PREVENTING OR TREATING DIABETES CONTAINING TENC1 EXPRESSION OR ACTIVITY SUPPRESSOR

CROSS-REFERENCE TO RELATED APPLICATIONS

This application is the U.S. national phase application filed under 35 U.S.C. §371 claiming benefit to International Patent Application No. PCT/KR2013/000288, filed on Jan. 14, 2013, which is entitled to priority under 35 U.S.C. §119(a)-(d) to Korea application nos. 10-2012-0009249, filed Jan. 30, 2012 and 10-2013-0004101, filed Jan. 14, 2013, each of which application is hereby incorporated herein by reference in its entirety.

TECHNICAL FIELD

The present invention relates to a pharmaceutical composition for preventing or treating diabetes or complications of diabetes which contains an inhibitor of expression or activity of TENC1 (Tensin like C1 domain containing phosphatase) as an active ingredient, and more specifically, to a pharmaceutical composition for preventing or treating diabetes or complications of diabetes which suppresses phosphorylation of IRS-1 (insulin receptor substrate-1) or degradation of IRS-1 due to a PTPase activity of TENC1.

BACKGROUND ART

Diabetes mellitus is a type of metabolic disease that causes an insufficient secretionary amount of insulin or a dysfunction thereof, and is characterized by hyperglycemia (having a high blood glucose level). Hyperglycemia causes several symptoms and signs, and glucose to be excreted in urine. In addition, as time passes, vascular disorders and dysfunctions in nerves, kidneys, retinas, and the like are caused, which results in death.

There are two types of diabetes: type 1 and type 2. Type 1 diabetes is called "juvenile diabetes" and occurs when no insulin is produced. Type 2 diabetes is caused by a relative lack of insulin and is characterized by insulin resistance (cells do not process glucose efficiently due to a degradation in a function of insulin that lowers a blood glucose level). Type 2 diabetes is thought to mainly result from environmental factors such as a high-calorie, a high-fat, and a high-protein diet present in a westernized diet, lack of exercise, and stress. Besides the environmental factors, diabetes may be caused by a defect of a specific gene, pancreatic surgery, infection, or drugs.

Recently, due to a westernized diet, stress, lack of exercise, and the like, chronic and life-style related adult diseases such as arteriosclerosis, hypertension, and diabetes have been increasing. In particular, in Korea, the prevalence of diabetes is consistently increasing: less than 1% of the population in the 1970s, about 3% in the late 1980s, and 5 to 8% in the 1990s. Accordingly, up to now, various types of therapeutic agents for diabetes have been developed but a satisfactory treating method or medicine has not been developed yet.

The insulin resistance, which is a feature of type 2 diabetes, is caused by a defect of insulin secretion itself and decrease in insulin signaling. Accordingly, recently, a method of treating diabetes by increasing insulin signaling has been newly proposed. For this purpose, a method of suppressing expression of proteins such as PTP1B (protein tyrosine phosphatase 1B) that inhibits a function of an insulin receptor is under development. However, in type 2 diabetes, a problem in insulin signaling is generally caused by degradation of a function (a decrease in the amount of protein and tyrosine phosphorylation of IRS-1) of IRS-1 (insulin receptor substrate-1) rather than a functional degradation of the insulin receptor. Accordingly, a protein capable of regulating the function of IRS-1 is important since it can be a target for treating diabetes and complications associated with diabetes. However, a protein that directly influences as PTPase (protein tyrosine phosphate) of IRS-1 in association with diabetes has not been reported yet. A case in which such PTPase regulates both an amount of protein and phosphorylation of IRS-1 has not been reported yet.

In this way, a protein capable of regulating a decrease in the amount of protein and phosphorylation of IRS-1 can be an effective target of a therapeutic agent for diabetes or complications of diabetes. Therefore, discovering such a target protein and development of a therapeutic agent for diabetes or complications of diabetes using the same are necessary.

DISCLOSURE

Technical Problem

In view of the above-described problems in the related art, the present invention provides a pharmaceutical composition for preventing or treating diabetes or complications of diabetes which contains an inhibitor of expression or activity of TENC1 (Tensin like C1 domain containing phosphatase) as an active ingredient. In addition, the present invention provides a method of screening an inhibitor of expression or activity of TENC1. The method includes culturing cells expressing TENC1 (Tensin like C1 domain containing phosphatase) along with a test substance or no test substance, and measuring the degree of expression or activity of TENC1 in the cells However, the scope of the present invention is not limited to the above-described objects, and other unmentioned objects may be clearly understood by those skilled in the art from the following descriptions.

Technical Solution

According to an aspect of the present invention, there is provided a pharmaceutical composition for preventing or treating diabetes or complications of diabetes which contains an inhibitor of expression or activity of TENC1 (Tensin like C1 domain containing phosphatase) as an active ingredient.

The expression inhibitor may be si6 or si7 which is siRNA.

The activity inhibitor may be ursolic acid.

The TENC1 may include an amino acid sequence of SEQ ID NO. 1.

The TENC1 may have a PTPase (protein tyrosine phosphate) activity.

The TENC1 may use IRS-1 (insulin receptor substrate-1) as a substrate.

The complications of diabetes may be selected from the group consisting of muscular atrophy, diabetic retinopathy, diabetic cataracts, diabetic nephropathy, diabetic neuropathy, heart disease, cancer, osteoporosis, renal disease, sexual dysfunction, skin disease, hypertension, arteriosclerosis, stroke, or atherosclerosis.

The composition may suppress IRS-1 degradability and/or dephosphorylation of TENC1.

According to another aspect of the present invention, there is provided a method of screening an inhibitor of expression or activity of TENC1 to treat or prevent diabetes or complications of diabetes, the method including:

culturing cells expressing TENC1 (tensin like C1 domain containing phosphatase) along with a test substance or no test substance; and measuring the degree of expression or activity of TENC1 in the cells.

The test substance may be selected from the group consisting of a chemical substance, a microbial culture solution or extract, a nucleic acid, an antibody, an aptamer, and a natural extract.

The measuring of the degree of expression of TENC1 may be performed by RT-PCR (real time-polymerase chain reaction) or Western blotting processes.

In the measuring of degree of the activity of TENC1, a PTPase activity of TENC1 or a degree of binding of TENC1 and IRS-1 may be measured.

Advantageous Effects

The present invention has verified that a PTPase activity of TENC1 suppresses phosphorylation of IRS-1 or directly degrades IRS-1 so that a glucose absorption decrease and muscular atrophy are caused, thereby proposing a new target for treating diabetes. Therefore, according to the present invention, a pharmaceutical composition, for preventing or treating diabetes or complications of diabetes containing an inhibitor of expression or activity of TENC1 as an active ingredient, suppresses dephosphorylation and degradation of IRS-1 caused by TENC1 and is able to effectively prevent a glucose absorption decrease and muscular atrophy due to a decrease of IRS-1. Therefore, the composition is expected to be widely applied to prevent and/or treat diabetes or complications of diabetes. Also, when a method of screening an inhibitor of expression or activity of TENC1 according to the present invention is used, the development of an agent that activates an IRS-1 mechanism and effectively prevents and/or treats diabetes or complications of diabetes can be expected.

DESCRIPTION OF DRAWINGS

FIG. 1 is a diagram illustrating the result obtained by determining an increase of TENC1 expression in a db/db mouse.

FIG. 3 is a diagram illustrating the result obtained by measuring an ability of TENC1 to suppress phosphorylation of an insulin receptor and IRS-1.

FIG. 16 is a diagram illustrating the result confirming that activity suppression of TENC1 inhibits dephosphorylation and degradation of IRS-1.

MODES OF THE INVENTION

Figure 2:
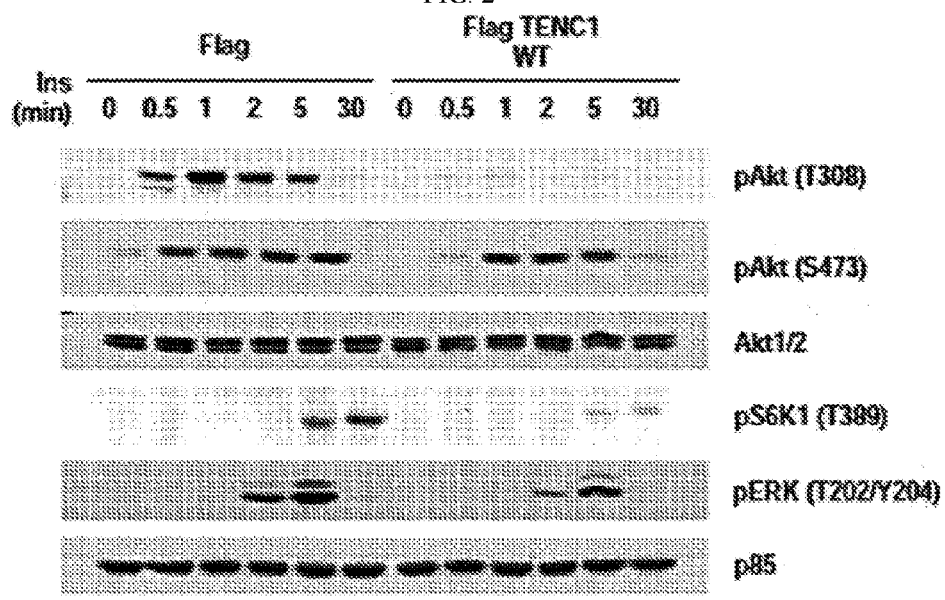
FIG. 2 is a diagram illustrating the result obtained by measuring an ability of TENC1 to suppress phosphorylation of Akt and ERK1/2.

The inventors studied a target protein that may be effectively used to treat diabetes by regulating functional degradation of IRS-1 (insulin receptor substrate-1), and thereby the present invention was completed.

Since a protein such as PTP1B (protein tyrosine phosphatase 1B) that has recently entered the spotlight as a target for treating diabetes acts in an insulin receptor, its role in glucose absorption was identified, but no effect was identified in a muscle mass decrease that is generally caused along with diabetes. Therefore, in order to screen a target of a therapeutic agent that may treat diabetes and the muscular atrophy that occurs with diabetes, the inventors analyzed a protein that is expressed more in a muscle of a diabetes-induced mouse than in a normal mouse, and thus, TENC1 protein (SEQ ID NO. 1) was screened.

An example of the present invention verified that TENC1 suppresses phosphorylation of IRS-1, and at the same time, suppresses a function of IRS by degrading IRS-1 (refer to FIGS. 4 to 10). Another example verified that TENC1 suppresses the function of IRS-1 so that muscular atrophy is caused (refer to FIGS. 11 to 13). Still another example of the present invention verified that an IRS-1 sub-signal increase and muscular atrophy caused by diabetes may be suppressed by suppressing TENC1 expression (refer to FIG. 15).

Still another example of the present invention verified that dephosphorylation of IRS-1 and degradation of IRS-1 may be inhibited by suppressing TENC1 activity (refer to FIG. 16).

Based on the above results, it was confirmed that TENC1 can be used as a target protein for treating diabetes or complications of diabetes and an inhibitor of expression or activity of TENC1 may be used as an effective agent for treating or preventing diabetes or complications of diabetes. Accordingly, the present invention provides a pharmaceutical composition for preventing or treating diabetes or complications of diabetes which contains an inhibitor of expression or activity of TENC1 (Tensin like C1 domain containing phosphatase) as an active ingredient. Examples of the complications of diabetes include muscular atrophy, diabetic retinopathy, diabetic cataracts, diabetic nephropathy, diabetic neuropathy, heart disease, cancer, osteoporosis, renal disease, sexual dysfunction, skin disease, hypertension, arteriosclerosis, stroke, atherosclerosis, and the like, but the complications are not limited thereto, as long as it can be caused by diabetes.

Also, the present invention provides a method of screening an inhibitor of expression or activity of TENC1 that may be used to prevent or treat diabetes or complications of diabetes. The method includes culturing cells expressing TENC1 (Tensin like C1 domain containing phosphatase) along with a test substance or no test substance, and measuring a degree of expression or activity of TENC1 in the cells. A method of measuring the degree of expression of TENC1 includes RT-PCR, Western blotting, or the like, but the method is not limited thereto, as long as it measures an amount of mRNA or protein. Also, a method of measuring the degree of activity of TENC1 measures a PTPase activity of TENC1 or a degree of binding of TENC1 and IRS-1. However, the method is not limited thereto. The test substance may be selected from the group consisting of a chemical substance, a microbial culture solution or extract, a nucleic acid, an antibody, an aptamer, and a natural extract, but the substance is not limited thereto.

The pharmaceutical composition of the present invention may include a pharmaceutically acceptable carrier. The pharmaceutically acceptable carrier may include a normal saline, a polyethylene glycol, ethanol, a vegetable oil, isopropyl myristate, or the like, but the carrier is not limited thereto.

Another aspect of the present invention provides a method of treating diabetes by administering a pharmaceutically effective dose of the pharmaceutical composition containing an inhibitor of expression or activity of TENC1 as an active ingredient to a subject. The term "subject" in the present invention refers to a target needing treatment of diseases, and more specifically, mammals such as humans or non-human apes, mice, rats, dogs, cats, horses, and cows. Also, in the present invention, it is apparent to those skilled in the art that a range of the pharmaceutically effective dose is variously adjusted depending on a patient's body weight, age, gender, health condition, diet, administration time, administration method, excretion rate, severity of the disease, and the like.

A preferred dosage of the pharmaceutical composition of the present invention varies depending on patient's condition, body weight, degree of the disease, drug form, administration route, and duration, but it may be appropriately selected by those skilled in the art. However, administration is performed for a day, preferably, 0.001 to 100 mg/body weight (kg), and more preferably, 0.01 to 30 mg/body weight (kg). Administration may be performed once a day or may be divided into several times. The inhibitor of expression or activity of TENC1 of the present invention may be included in an amount of 0.0001 to 10 wt %, and preferably, 0.001 to 1 wt %, with respect to a total weight of a total composition.

The pharmaceutical composition of the present invention may be administered to mammals such as a rat, mouse, livestock, and human via various routes. The administration method is not limited, and administration may be performed, for example, by oral, rectal, or intravenous, intramuscular, subcutaneous, intrauterine subdural, or intracerebroventricular injections.

Hereinafter, exemplary examples of the present invention will be described for promoting an understanding of the invention. However, the following examples are provided to easily understand the present invention and the scope of the present invention is not limited to the following examples.

EXAMPLE

Example 1

Screening of Protein Associated with Diabetes

A protein having an SH2 (Src homology 2) domain is known to be important in delivering a signal from a receptor. Therefore, in order to screen a novel protein associated with diabetes, the inventors performed screening of a protein, which has an SH2 domain and is expressed more than in a normal mouse, from a muscle of a 10-week-old male db/db mouse from which a leptin receptor is removed to induce obesity and diabetes, by quantitative real-time PCR. In order to perform PCR, forward primer 5'-CTCAGTG-GAGTTTGTTTTCTCCTC-3' (SEQ ID NO. 2) of TENC1, reverse primer 5'-GCTGATTGAAGTTTTCATAGGAGTC-3' (SEQ ID NO. 3) of TENC1, p85a forward primer 5'-GGC-GATTACACTCTTACACTAAGGA-3' (SEQ ID NO. 4), and p85a reverse primer 5'-GAGTTGAAGGTTAATGGATCA-GAGA-3' (SEQ ID NO. 5) were used. The result was shown in FIG. 1.

As illustrated in FIG. 1, it was confirmed that mRNA of TENC1 significantly increased more than three times in a skeletal muscle of the db/db mouse (FIG. 1A), and an amount of a protein of TENC1 also increased (FIG. 1B). It was well-known that type 2 diabetes causes sarcopenia. Based on the above result, it was confirmed that TENC1 was associated with pathological symptoms expressed in association with type 2 diabetes.

Example 2

Determine Influence of TENC1 on Insulin Mechanism

In most type 2 diabetes patients, a function of insulin that lowers a blood glucose level decreases, and thereby cells are unable to effectively process the glucose. In order to determine an influence of TENC1 on an insulin mechanism, TENC1 was overexpressed in HEK293 cell lines in which expression of TENC1 is low, and then phosphorylation of proteins associated with the insulin mechanism was determined by Western blotting. The result was shown in FIG. 2.

As illustrated in FIG. 2, it was confirmed that phosphorylation of Akt (protein kinase B) T308 and ERK1/2 (extracellular signal-regulated kinase) stimulated by the insulin was suppressed by TENC1.

Since phosphorylation of Akt and ERK1/2 is caused by tyrosine phosphorylation of the insulin receptor and IRS-1 (insulin receptor substrate-1), it was determined whether phosphorylation of the insulin receptor and IRS-1 was suppressed by TENC1 using the same method as described above. The result was shown in FIG. 3.

As illustrated in FIG. 3A, it was confirmed that TENC1 suppressed phosphorylation of IRS-1 by about 50% but had no influence on phosphorylation of the insulin receptor. In addition, in order to determine whether a phosphorylation inhibitory ability of TENC1 is caused by an activity of protein tyrosine phosphatase (PTPase), a TENC1 CS variant in which a cysteine at amino acid position 231 was substituted for a serine was prepared. The TENC1 CS variant is a mutant that more reliably binds to the substrate than normal TENC1 but has no catalytic action. Using the TENC1 CS variant, phosphorylation of IRS-1 was determined using the same method as described above. The result was shown in FIG. 3B.

As illustrated in FIG. 3B, it was confirmed that phosphorylation of IRS-1 was restored again when the TENC1 CS is used. Based on the above results, it was confirmed that TENC1 suppressed phosphorylation of IRS-1, suppressed phosphorylation of Akt and ERK1/2, and thereby suppressed the insulin mechanism.

Example 3

Determine IRS-1 Phosphorylation Inhibition Mechanism of TENC1

In order to determine a mechanism of TENC1 that suppresses phosphorylation of IRS-1, immunoprecipitation was performed using IRS-1. In a control experiment, vanadate, which is an analogue of phosphotyrosine and binds to a PTPase domain to inhibit the PTPase activity, was used. The result was shown in FIGS. 4 and 5.

Figure 4:
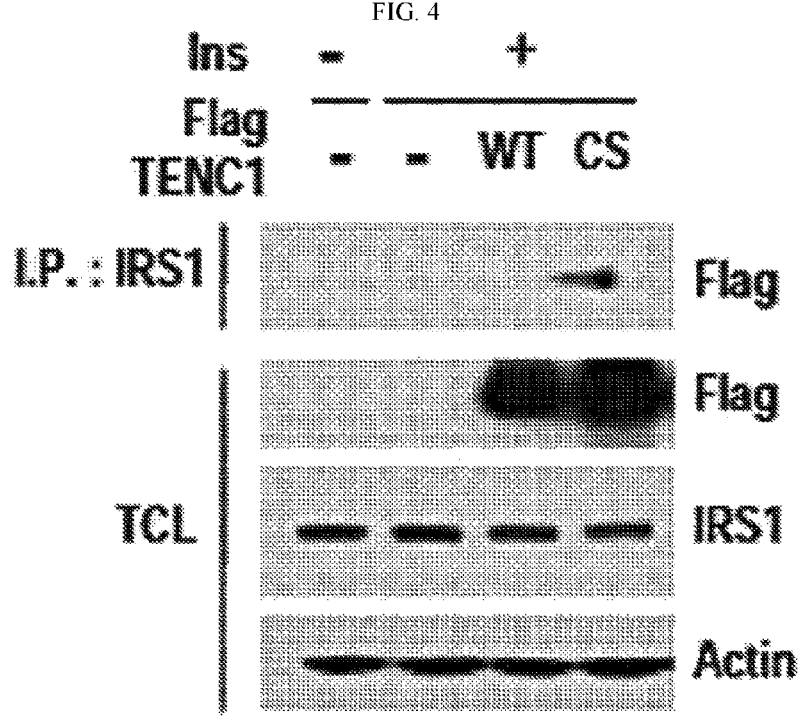
FIG. 4 is a diagram illustrating the result obtained by determining the binding of TENC1 and IRS-1.
Figure 5:
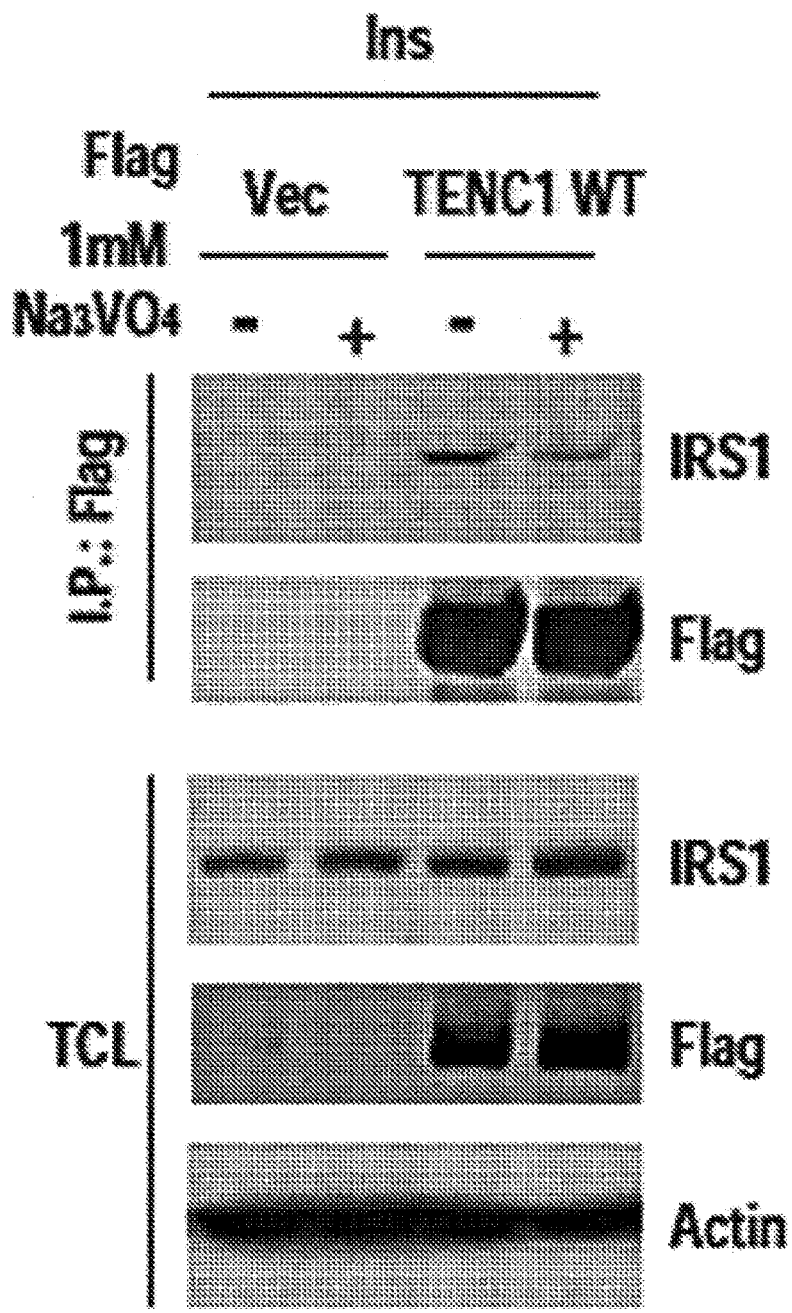
FIG. 5 is a diagram illustrating the results obtained by determining the binding of IRS-1 and a PTPase domain of TENC1.
Figure 6:
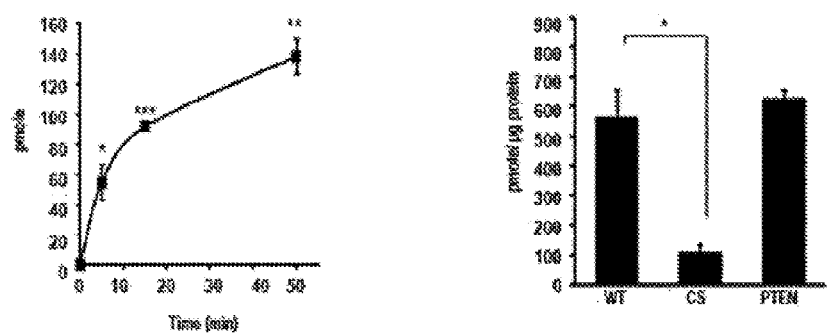
FIG. 6 is a diagram illustrating the result obtained by measuring a PTPase enzyme activity of TENC1.

As illustrated in FIG. 4, it was confirmed that the TENC1 CS variant was more reliably bound to IRS-1 than TENC1 WT. Also, as illustrated in FIG. 5, it was confirmed that, when the vanadate was not treated, TENC1 WT was bound to IRS-1, but when the vanadate was treated, binding with IRS-1 decreased. Based on the above result, it was confirmed that IRS-1 was bound to the PTPase domain of TENC1 in competition with the vanadate. Therefore, it was confirmed that IRS-1 was directly bound to the PTPase domain as a substrate of TENC1.

In addition, in order to measure the PTPase activity of TENC1, first, TENC1 was separated from HEK293 cell lines using a Flag immunoprecipitation/Flag peptide elution system. Then, the PTPase activity of the separated TENC1 was measured over time, using peptides having phosphotyrosine. The PTPase activity was analyzed by a malachite green assay method. As a control group, PTEN (a phosphatase and tensin homolog) or the TENC1 CS variant was used. The result was shown in FIG. 6.

As illustrated in FIGS. 6A and 6B, it was confirmed that the PTPase activity of TENC1 was similar to that of PTEN, and there was no PTPase activity in the TENC1 CS variant. Based on the above result, it was confirmed that TENC1 was bound to IRS-1 through the PTPase activity to suppress phosphorylation. Also, the above result means that TENC1 suppresses phosphorylation of IRS-1 to influence the onset of diabetes.

Example 4

Determine IRS-1 Degradation Mechanism of TENC1

In order to know a physiological function of TENC1, TENC1 was overexpressed in L6 myotube (muscle cell) that plays a main role in IRS-1, using an adenovirus. Using the same method as in Example 1, the quantitative PCR was performed and it was confirmed that TENC1 mRNA was increased eightfold to tenfold in the myotube. Then, using the same method as in Example 2, phosphorylation of proteins associated with IRS-1 was determined. The result was shown in FIG. 7.

Figure 7:
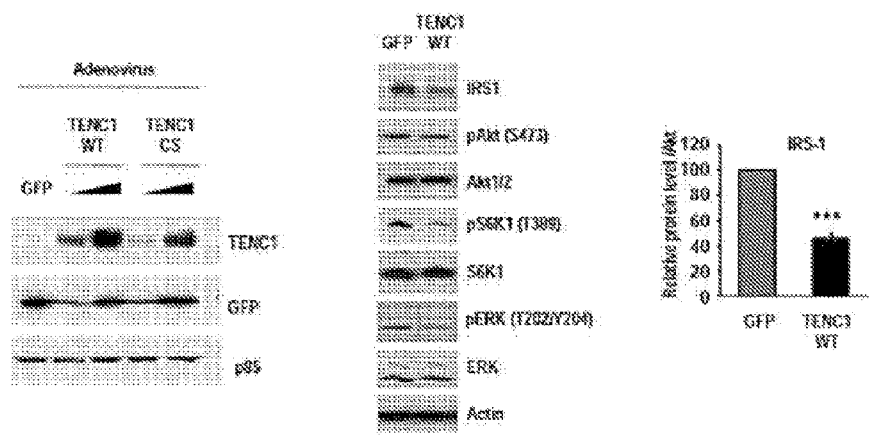
FIG. 7 is a diagram illustrating the result obtained by measuring phosphorylation of proteins associated with IRS-1 in a muscle when TENC1 is expressed.

As illustrated in FIG. 7, it was confirmed that phosphorylation of Akt, S6K1, and ERK1/2 regulated by IRS-1 was suppressed in the cells in which TENC1 was overexpressed (FIGS. 7A and 7B). However, it was confirmed that an amount of protein of IRS-1 also decreased (FIG. 7C).

In order to determine whether an amount of IRS-1 is decreased due to suppressed gene expression, an mRNA amount of IRS-1 was quantified using IRS-1 forward primer (SEQ ID NO. 6) and reverse primer (SEQ ID NO. 7) by quantitative PCR. The result was shown in FIG. 8.

Figure 8:
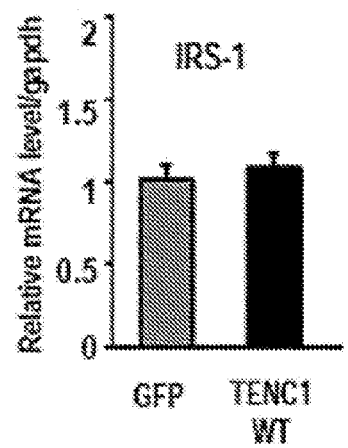
FIG. 8 is a diagram illustrating the result obtained by measuring an amount of mRNA of IRS-1 when TENC1 is expressed.

As illustrated in FIG. 8, it was confirmed that the amount of mRNA of IRS-1 was not decreased. Based on the above result, it was confirmed that a decrease in the amount of protein of IRS-1 had occurred not because of gene expression in a transcription phase but because of a phase after transcription.

Accordingly, in order to determine the reason for the decrease of IRS-1, it was determined whether TENC1 influences a ubiquitin proteasome pathway or serine phosphorylation of IRS-1 by Western blotting. In order to determine whether TENC1 influences a protein-degrading mechanism, MG132, which is an inhibitor of a protein-degrading enzyme (proteasome), was treated. The result was shown in FIG. 9.

Figure 9:
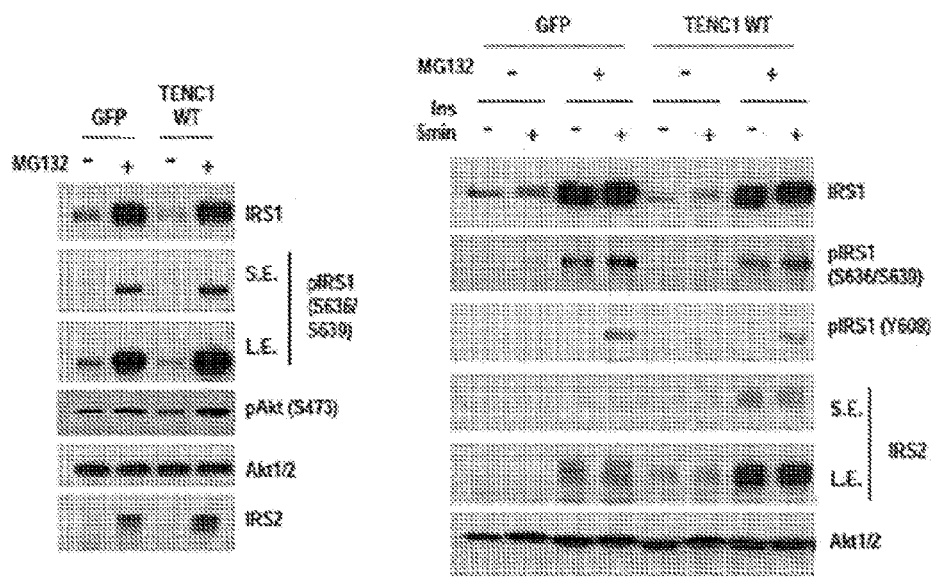
FIG. 9 is a diagram illustrating the result obtained by measuring serine phosphorylation of IRS-1 when TENC1 is expressed.

As illustrated in FIG. 9, it was confirmed that, when the insulin was not treated (FIG. 9A) and when the insulin was treated (FIG. 9B), the decreased amount of IRS-1 was restored if MG132 was treated, and in the cells in which the amount of IRS-1 was restored by treating MG132, there was no difference of serine phosphorylation of IRS-1, but phosphorylation of IRS-1 was suppressed. Based on the above result, it was confirmed that TENC1 degrades IRS-1 or suppresses phosphorylation thereof to influence the mechanism of IRS-1.

In order to determine whether the PTPase activity of TENC1 influences degradation of IRS-1, vanadate was treated to determine whether degradation of IRS-1 is suppressed by Western blotting. The result was shown in FIG. 10.

Figure 10:
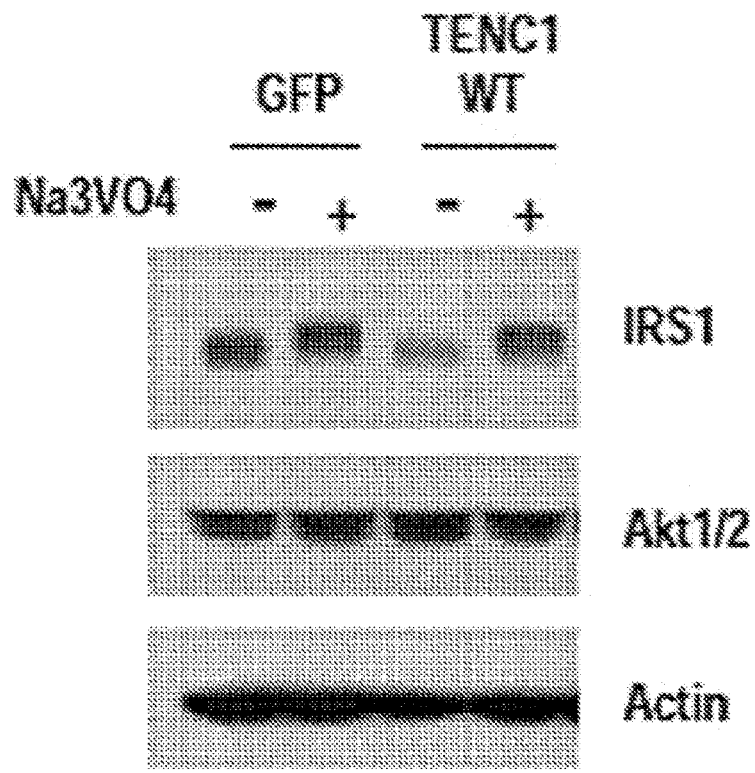
FIG. 10 is a diagram illustrating the result obtained by determining an influence of a PTPase activity of TENC1 on IRS-1 degradation.

As illustrated in FIG. 10, it was confirmed that, when the vanadate was treated, degradation of IRS-1 was suppressed. It was understood that an activity of TENC1 was directly involved in IRS-1 degradation.

Example 5

Determine Associative Relation Between TENC1 and Muscular Atrophy

An increase in a protein amount of IRS-2 and a decrease in PI3K/Akt/mTORC1 signal transduction due to a decrease in an amount of protein of IRS-1 are observed in muscular atrophy caused by glucocorticoid and muscular atrophy of acute diabetes caused by streptozotocin (STZ). Therefore, in order to determine whether TENC1 causes atrophy of a myotube, the experiment was prepared such that green fluorescent protein (GFP) was expressed in the myotube using adenovirus, TENC1 WT or TENC1 CS was overexpressed, and a diameter of the myotube was measured using fluorescent light. The result was shown in FIG. 11.

Figure 11:
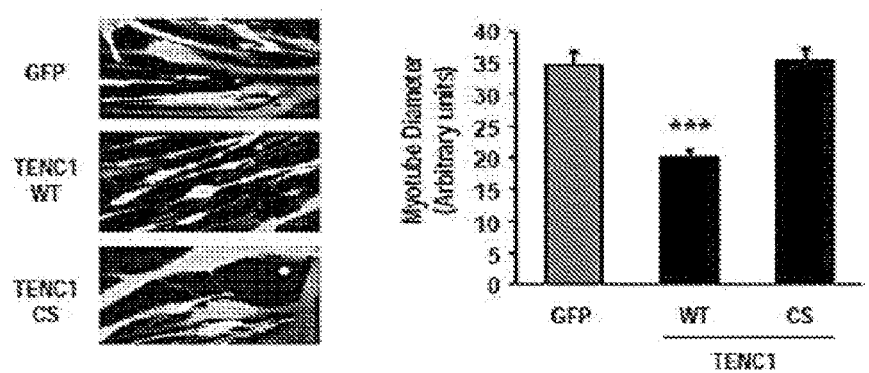
FIG. 11 is a diagram illustrating the result obtained by determining an ability to cause muscular atrophy in vitro dependent on an enzyme activity of TENC1.

As illustrated in FIG. 11, it was confirmed that sizes of the cells in which TENC1 was overexpressed decreased by about 40%, compared to the cells in which TENC1 CS was overexpressed. The above result means that TENC1 is associated with muscular atrophy caused by diabetes.

It was known that the ubiquitin proteasome pathway in the muscular atrophy degrades myofibrillar proteins such as a myosin heavy chain (MYH) which is a main component of skeletal muscle. Therefore, an experiment was performed to determine whether TENC1 influences the ubiquitin proteasome pathway to decrease MYH. The result was shown in FIG. 12.

Figure 12:
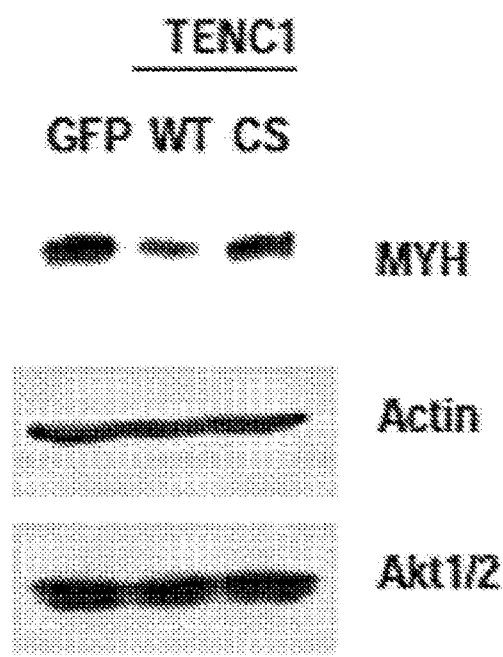
FIG. 12 is a diagram illustrating the result obtained by measuring an ability of TENC1 to decrease MYH.

As illustrated in FIG. 12, it was confirmed that TENC1 degraded MYH according to an activity of PTPase by Western blotting. Based on the above result, it was confirmed that TENC1 degraded IRS-1 to suppress an Akt/S6K1 mechanism so that the muscular atrophy may be caused.

Mammalian cells include three types of FoxO (Forkhead Box O) proteins: FoxO1, FoxO3, and FoxO4. Among them, phosphorylation of FoxO1 and FoxO3 is essential for muscular atrophy caused by the glucocorticoid. In particular, activated FoxO3 stimulates expression of genes that play an important role in muscular atrophy, that is, various atrogenes, to cause the muscular atrophy. Therefore, it was determined whether TENC1 influences phosphorylation of FoxO1 and FoxO3 by Western blotting. The result was shown in FIG. 13.

Figure 13:
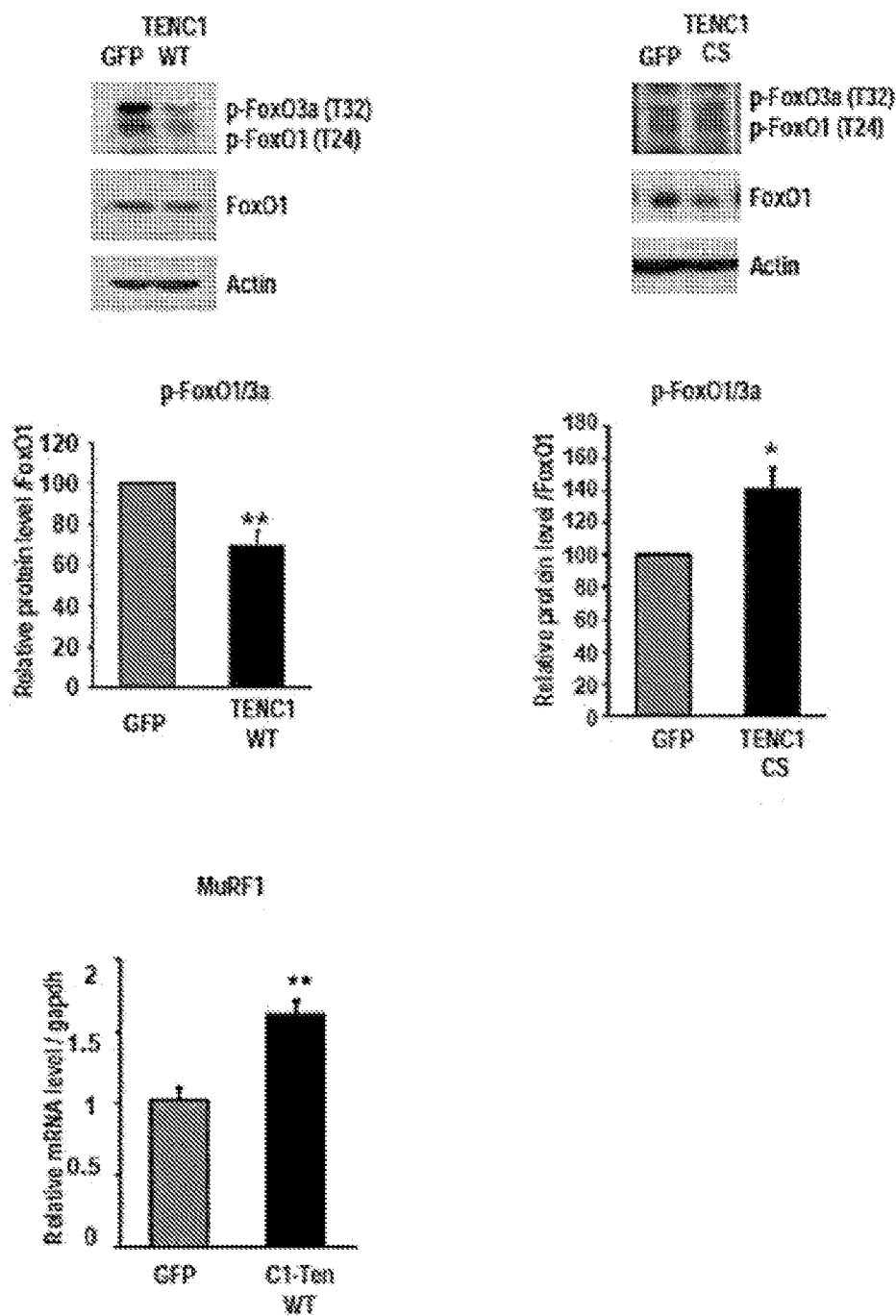
FIG. 13 is a diagram illustrating the result obtained by determining an influence of TENC1 on phosphorylation of FoxO protein.

As illustrated in FIG. 13, in the myotube (FIG. 13A) in which TENC1 was overexpressed, phosphorylation of FoxO1/3a decreased. In the myotube (FIG. 13B) in which TENC1 CS was overexpressed, an amount of protein of FoxO1 decreased and an amount of phosphorylated FoxO1/3a relatively increased. In addition, expression of MuRF1 (muscle RING finger 1) regulated by FoxO proteins increased in the myotube in which TENC1 was overexpressed (FIG. 13C). Based on the above result, it was confirmed that TENC1 degraded IRS-1 to activate FoxO proteins so that atrophy of the myotube may be caused.

Example 6

Determine Muscular Atrophy Caused by TENC1

Figure 14:
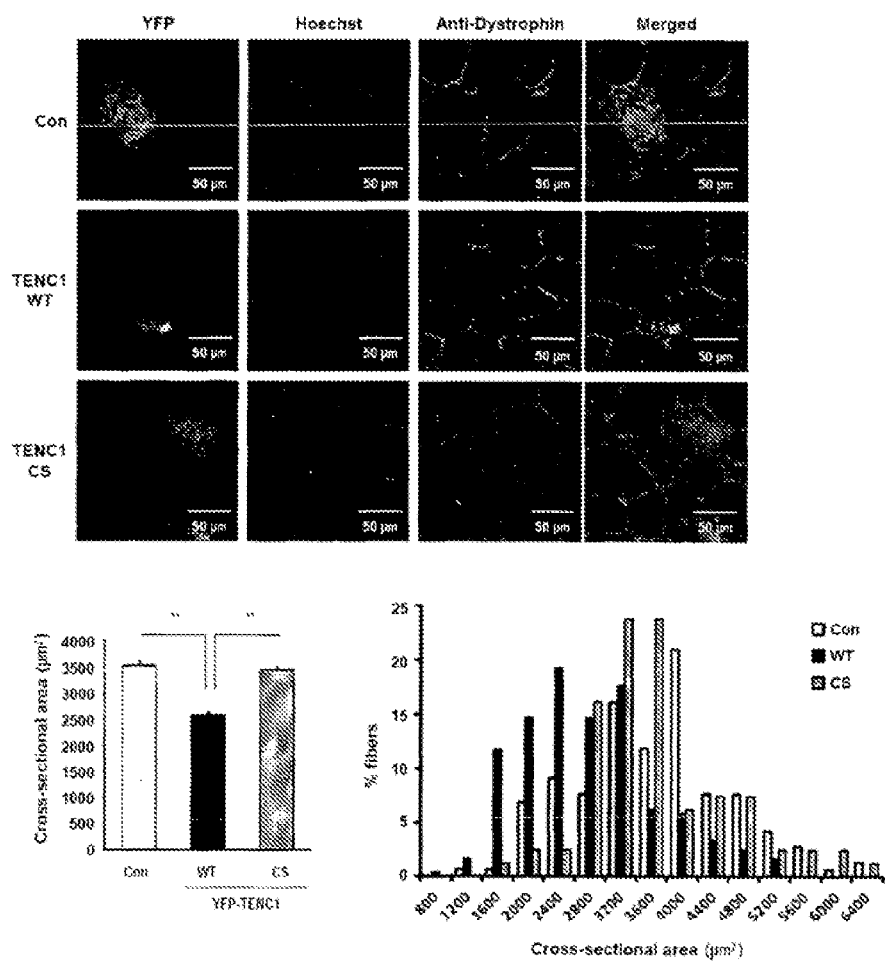
FIG. 14 is a diagram illustrating the result obtained by determining an ability to cause muscular atrophy in vivo dependent on an enzyme activity of TENC1.

In order to determine whether TENC1 causes muscular atrophy in vivo, TENC1 to which YFP (yellow fluorescent protein) is bound was injected into a tibialis anterior muscle of the mouse by electroporation. Then, a size change of a myofiber was measured using the YFP. The result was shown in FIG. 14.

As illustrated in FIGS. 14A, 14B, and 14C, it was confirmed that a cross-sectional area (CSA) of the muscle into which TENC1 was injected decreased by about 25% after 12 days. However, it was confirmed that TENC1 CS did not cause muscular atrophy. Based on the above result, it was confirmed that TENC1 may cause muscular atrophy in vivo due to the PTPase activity.

Example 7

Determine Effect of Suppressing TENC1 Expression

In order to determine whether TENC1 may be used as a target for treating diabetes, si6 and si7, which are siRNA binding specifically to TENC1, were used. It was determined, when an amount of TENC1 decreased, IRS-1 degradation caused by a glucocorticoid is restored to prevent muscular atrophy of the myotube. siRNA was introduced into L6 myotube using a DeliverX Plus siRNA transfection kit (Panomics). The result was shown in FIG. 15.

Figure 15:
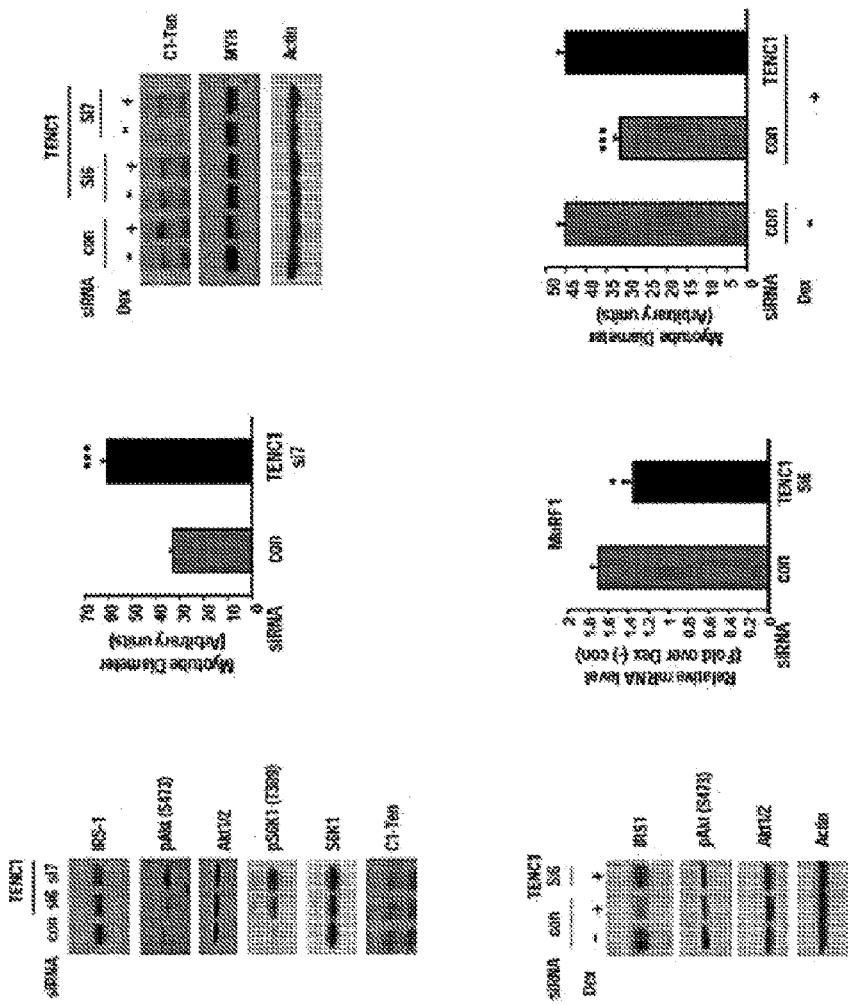
FIG. 15 is a diagram illustrating that suppression of TENC1 expression causes muscle hypertrophy and suppression of IRS-1 degradation inhibits muscular atrophy.

As illustrated in FIG. 15, it was confirmed that, when siRNA was used to inhibit expression of TENC1, an MYH decrease caused by the glucocorticoid was effectively suppressed (FIG. 15C). However, it was understood that si7 strongly inhibits expression of TENC1 to cause muscle hypertrophy through activation of sub-proteins of IRS-1 (FIGS. 15A and 15B). In addition, it was confirmed that stimulation of MuRF1 and IRS-1 degradation (FIG. 15D) caused by the glucocorticoid were restored (FIG. 15B), and muscular atrophy was suppressed (FIG. 15F).

Example 8

Determine Effect of Suppressing TENC1 Activity

It was reported that ursolic acid suppresses muscular atrophy and causes muscle hypertrophy. However, a target or an operating mechanism thereof has not been clearly identified yet.

Therefore, the inventors determined whether ursolic acid is able to regulate an activity by targeting TENC1 through the following experiment.

Specifically, TENC1 proteins that were separated using the same method as in Example 3 were incubated along with 20 µM of ursolic acid and then a change in the PTPase activity was measured by the malachite green assay (in this case, the vanadate was used as a control group). As a result, it was confirmed that the PTPase activity of TENC1 was inhibited by 60% or more (FIG. 16A).

In addition, using the same method as in Example 2, when the cells (HEK293 cell lines) in which TENC1 and IRS-1 were overexpressed were cultured along with a test substance, tyrosine phosphorylation of IRS-1 increased and thereby it was confirmed that dephosphorylation of IRS-1 caused by TENC1 was inhibited at a cellular level (FIG. 16B).

In addition, ursolic acid was added to the myotube (muscle cell) in which TENC1 was overexpressed, and then a degree of degradation of IRS-1 protein was determined by Western blotting. As a result, when a concentration of ursolic acid increases, IRS-1 is restored to a level similar to a control group (cells in which TENC1 was not overexpressed). Therefore, it was confirmed that IRS-1 degradation caused by the activity of TENC1 was suppressed by ursolic acid (FIG. 16C).

Based on the above results, an activity inhibitor of TENC1 such as ursolic acid inhibits dephosphorylation of IRS-1 and degradation of IRS-1 caused by the activity of TENC1. Therefore, it was confirmed that a decrease in glucose absorption, muscular atrophy, and the like caused by a decrease of IRS-1 may be effectively prevented. As a result, it is understood that the activity inhibitor of TENC1 may be effectively used to treat or prevent diabetes.

The inhibitor of expression or activity of TENC1 of the present invention suppresses dephosphorylation and degradation of IRS-1 caused by TENC1 and is able to prevent a glucose absorption decrease and muscular atrophy caused by a decrease of IRS-1, so it can be developed as an agent that prevents and/or treat diabetes or complications of diabetes. In addition, the method of screening proposed in the present invention provides TENC1 as a new target compound to overcome a limitation of an existing therapeutic agent. Therefore, the present invention can be usefully used to develop an agent having a new mechanism for preventing and/or treating diabetes or complications of diabetes.

The above description of the invention is only exemplary, and it will be understood by those skilled in the art that various modifications can be made without departing from the scope of the present invention and without changing essential features. Therefore, the above-described examples should be considered in a descriptive sense only and not for purposes of limitation.

The invention claimed is:

1. A method for treating type 2 diabetes or complications of type 2 diabetes comprising administering to a subject in need thereof a pharmaceutical composition comprising:
an inhibitor of expression of TENC1 (Tensin like C1 domain containing phosphatase) as an active ingredient, wherein the inhibitor of expression of TENC1 is an siRNA comprising a sequence of SEQ ID NO. 8 or SEQ ID NO. 9.

2. The method of claim 1, wherein the TENC1 includes an amino acid sequence of SEQ ID NO. 1.

3. The method of claim 1, wherein the TENC1 includes a PTPase (protein tyrosine phosphate) activity.

4. The method of claim 1, wherein the TENC1 uses IRS-1 (insulin receptor substrate-1) as a substrate.

5. The method of claim 1, wherein the complications of diabetes are selected from the group consisting of muscular atrophy, diabetic retinopathy, diabetic cataract, diabetic nephropathy, diabetic neuropathy, heart disease, cancer, osteoporosis, renal disease, sexual dysfunction, skin disease, hypertension, arteriosclerosis, stroke, and atherosclerosis.

6. The method of claim 1, wherein the method suppresses degradation of IRS-1 by TENC1.

7. The method of claim 1, wherein the method suppresses IRS-1 dephosphorylation of TENC1.

* * * * *

SEQUENCE LISTING

<160> NUMBER OF SEQ ID NOS: 9

<210> SEQ ID NO 1
<211> LENGTH: 1409
<212> TYPE: PRT
<213> ORGANISM: Homo sapiens

```
<400> SEQUENCE: 1

Met Lys Ser Ser Gly Pro Val Glu Arg Leu Leu Arg Ala Leu Gly Arg
1               5                   10                  15

Arg Asp Ser Ser Arg Ala Ala Ser Arg Pro Arg Lys Ala Glu Pro His
            20                  25                  30

Ser Phe Arg Glu Lys Val Phe Arg Lys Pro Pro Val Cys Ala Val
            35                  40                  45

Cys Lys Val Thr Ile Asp Gly Thr Gly Val Ser Cys Arg Val Cys Lys
    50                  55                  60

Val Ala Thr His Arg Lys Cys Glu Ala Lys Val Thr Ser Ala Cys Gln
65                  70                  75                  80

Ala Leu Pro Pro Val Glu Leu Arg Arg Asn Thr Ala Pro Val Arg Arg
                85                  90                  95

Ile Glu His Leu Gly Ser Thr Lys Ser Leu Asn His Ser Lys Gln Arg
            100                 105                 110

Ser Thr Leu Pro Arg Ser Phe Ser Leu Asp Pro Leu Met Glu Arg Arg
            115                 120                 125

Trp Asp Leu Asp Leu Thr Tyr Val Thr Glu Arg Ile Leu Ala Ala Ala
    130                 135                 140

Phe Pro Ala Arg Pro Asp Glu Gln Arg His Arg Gly His Leu Arg Glu
145                 150                 155                 160

Leu Ala His Val Leu Gln Ser Lys His Arg Asp Lys Tyr Leu Leu Phe
                165                 170                 175

Asn Leu Ser Glu Lys Arg His Asp Leu Thr Arg Leu Asn Pro Lys Val
            180                 185                 190

Gln Asp Phe Gly Trp Pro Glu Leu His Ala Pro Pro Leu Asp Lys Leu
            195                 200                 205

Cys Ser Ile Cys Lys Ala Met Glu Thr Trp Leu Ser Ala Asp Pro Gln
    210                 215                 220

His Val Val Val Leu Tyr Cys Lys Gly Asn Lys Gly Lys Leu Gly Val
225                 230                 235                 240

Ile Val Ser Ala Tyr Met His Tyr Ser Lys Ile Ser Ala Gly Ala Asp
                245                 250                 255

Gln Ala Leu Ala Thr Leu Thr Met Arg Lys Phe Cys Glu Asp Lys Val
            260                 265                 270

Ala Thr Glu Leu Gln Pro Ser Gln Arg Arg Tyr Ile Ser Tyr Phe Ser
            275                 280                 285

Gly Leu Leu Ser Gly Ser Ile Arg Met Asn Ser Ser Pro Leu Phe Leu
    290                 295                 300

His Tyr Val Leu Ile Pro Met Leu Pro Ala Phe Glu Pro Gly Thr Gly
305                 310                 315                 320

Phe Gln Pro Phe Leu Lys Ile Tyr Gln Ser Met Gln Leu Val Tyr Thr
                325                 330                 335

Ser Gly Val Tyr His Ile Ala Gly Pro Gly Pro Gln Gln Leu Cys Ile
            340                 345                 350

Ser Leu Glu Pro Ala Leu Leu Leu Lys Gly Asp Val Met Val Thr Cys
            355                 360                 365

Tyr His Lys Gly Gly Arg Gly Thr Asp Arg Thr Leu Val Phe Arg Val
    370                 375                 380

Gln Phe His Thr Cys Thr Ile His Gly Pro Gln Leu Thr Phe Pro Lys
385                 390                 395                 400

Asp Gln Leu Asp Glu Ala Trp Thr Asp Glu Arg Phe Pro Phe Gln Ala
                405                 410                 415
```

```
Ser Val Glu Phe Val Phe Ser Ser Pro Lys Ile Lys Gly Ser
            420             425             430

Thr Pro Arg Asn Asp Pro Ser Val Ser Val Asp Tyr Asn Thr Thr Glu
            435             440             445

Pro Ala Val Arg Trp Asp Ser Tyr Glu Asn Phe Asn Gln His His Glu
        450             455             460

Asp Ser Val Asp Gly Ser Leu Thr His Thr Arg Gly Pro Leu Asp Gly
465             470             475             480

Ser Pro Tyr Ala Gln Val Gln Arg Pro Arg Gln Thr Pro Pro Ala
                485             490             495

Pro Ser Pro Glu Pro Pro Pro Pro Met Leu Ser Val Ser Ser Asp
            500             505             510

Ser Gly His Ser Ser Thr Leu Thr Thr Glu Pro Ala Ala Glu Ser Pro
            515             520             525

Gly Arg Pro Pro Pro Thr Ala Ala Glu Arg Gln Glu Leu Asp Arg Leu
            530             535             540

Leu Gly Gly Cys Gly Val Ala Ser Gly Gly Arg Gly Ala Gly Arg Glu
545             550             555             560

Thr Ala Ile Leu Asp Asp Glu Glu Gln Pro Thr Val Gly Gly Pro
                565             570             575

His Leu Gly Val Tyr Pro Gly His Arg Pro Gly Leu Ser Arg His Cys
            580             585             590

Ser Cys Arg Gln Gly Tyr Arg Glu Pro Cys Gly Val Pro Asn Gly Gly
            595             600             605

Tyr Tyr Arg Pro Glu Gly Thr Leu Glu Arg Arg Leu Ala Tyr Gly
            610             615             620

Gly Tyr Glu Gly Ser Pro Gln Gly Tyr Ala Glu Ala Ser Met Glu Lys
625             630             635             640

Arg Arg Leu Cys Arg Ser Leu Ser Glu Gly Leu Tyr Pro Tyr Pro Pro
                645             650             655

Glu Met Gly Lys Pro Ala Thr Gly Asp Phe Gly Tyr Arg Ala Pro Gly
            660             665             670

Tyr Arg Glu Val Val Ile Leu Glu Asp Pro Gly Leu Pro Ala Leu Tyr
            675             680             685

Pro Cys Pro Ala Cys Glu Glu Lys Leu Ala Leu Pro Thr Ala Ala Leu
690             695             700

Tyr Gly Leu Arg Leu Glu Arg Glu Ala Gly Glu Gly Trp Ala Ser Glu
705             710             715             720

Ala Gly Lys Pro Leu Leu His Pro Val Arg Pro Gly His Pro Leu Pro
            725             730             735

Leu Leu Leu Pro Ala Cys Gly His His Ala Pro Met Pro Asp Tyr
            740             745             750

Ser Cys Leu Lys Pro Pro Lys Ala Gly Glu Glu Gly His Glu Gly Cys
            755             760             765

Ser Tyr Thr Met Cys Pro Glu Gly Arg Tyr Gly His Pro Gly Tyr Pro
            770             775             780

Ala Leu Val Thr Tyr Ser Tyr Gly Gly Ala Val Pro Ser Tyr Cys Pro
785             790             795             800

Ala Tyr Gly Arg Val Pro His Ser Cys Gly Ser Pro Gly Glu Gly Arg
                805             810             815

Gly Tyr Pro Ser Pro Gly Ala His Ser Pro Arg Ala Gly Ser Ile Ser
            820             825             830
```

```
Pro Gly Ser Pro Pro Tyr Pro Gln Ser Arg Lys Leu Ser Tyr Glu Ile
        835                 840                 845

Pro Thr Glu Glu Gly Gly Asp Arg Tyr Pro Leu Pro Gly His Leu Ala
    850                 855                 860

Ser Ala Gly Pro Leu Ala Ser Ala Glu Ser Leu Glu Pro Val Ser Trp
865                 870                 875                 880

Arg Glu Gly Pro Ser Gly His Ser Thr Leu Pro Arg Ser Pro Arg Asp
                885                 890                 895

Ala Pro Cys Ser Ala Ser Ser Glu Leu Ser Gly Pro Ser Thr Pro Leu
            900                 905                 910

His Thr Ser Ser Pro Val Gln Gly Lys Glu Ser Thr Arg Arg Gln Asp
        915                 920                 925

Thr Arg Ser Pro Thr Ser Ala Pro Thr Gln Arg Leu Ser Pro Gly Glu
    930                 935                 940

Ala Leu Pro Pro Val Ser Gln Ala Gly Thr Gly Lys Ala Pro Glu Leu
945                 950                 955                 960

Pro Ser Gly Ser Gly Pro Glu Pro Leu Ala Pro Ser Pro Val Ser Pro
                965                 970                 975

Thr Phe Pro Pro Ser Ser Pro Ser Asp Trp Pro Gln Glu Arg Ser Pro
            980                 985                 990

Gly Gly His Ser Asp Gly Ala Ser  Pro Arg Ser Pro Val  Pro Thr Thr
            995                 1000                1005

Leu Pro  Gly Leu Arg His Ala  Pro Trp Gln Gly Pro  Arg Gly Pro
    1010                1015                1020

Pro Asp  Ser Pro Asp Gly Ser  Pro Leu Thr Pro Val  Pro Ser Gln
    1025                1030                1035

Met Pro  Trp Leu Val Ala Ser  Pro Glu Pro Pro Gln  Ser Ser Pro
    1040                1045                1050

Thr Pro  Ala Phe Pro Leu Ala  Ala Ser Tyr Asp Thr  Asn Gly Leu
    1055                1060                1065

Ser Gln  Pro Pro Leu Pro Glu  Lys Arg His Leu Pro  Gly Pro Gly
    1070                1075                1080

Gln Gln  Pro Gly Pro Trp Gly  Pro Glu Gln Ala Ser  Ser Pro Ala
    1085                1090                1095

Arg Gly  Ile Ser His His Val  Thr Phe Ala Pro Leu  Leu Ser Asp
    1100                1105                1110

Asn Val  Pro Gln Thr Pro Glu  Pro Pro Thr Gln Glu  Ser Gln Ser
    1115                1120                1125

Asn Val  Lys Phe Val Gln Asp  Thr Ser Lys Phe Trp  Tyr Lys Pro
    1130                1135                1140

His Leu  Ser Arg Asp Gln Ala  Ile Ala Leu Leu Lys  Asp Lys Asp
    1145                1150                1155

Pro Gly  Ala Phe Leu Ile Arg  Asp Ser His Ser Phe  Gln Gly Ala
    1160                1165                1170

Tyr Gly  Leu Ala Leu Lys Val  Ala Thr Pro Pro Pro  Ser Ala Gln
    1175                1180                1185

Pro Trp  Lys Gly Asp Pro Val  Glu Gln Leu Val Arg  His Phe Leu
    1190                1195                1200

Ile Glu  Thr Gly Pro Lys Gly  Val Lys Ile Lys Gly  Cys Pro Ser
    1205                1210                1215

Glu Pro  Tyr Phe Gly Ser Leu  Ser Ala Leu Val Ser  Gln His Ser
    1220                1225                1230
```

| | | | | | | | | | | |
|---|---|---|---|---|---|---|---|---|---|---|
| Ile | Ser | Pro | Ile | Ser | Leu | Pro | Cys | Cys | Leu | Arg | Ile | Leu | Ser | Lys |
| | 1235 | | | | 1240 | | | | | 1245 | | | | |

Asp Pro Leu Glu Glu Thr Pro Glu Ala Pro Val Pro Thr Asn Met
    1250                         1255                       1260

Ser Thr Ala Ala Asp Leu Leu Arg Gln Gly Ala Ala Cys Ser Val
    1265                         1270                       1275

Leu Tyr Leu Thr Ser Val Glu Thr Glu Ser Leu Thr Gly Pro Gln
    1280                         1285                       1290

Ala Val Ala Arg Ala Ser Ser Ala Ala Leu Ser Cys Ser Pro Arg
    1295                         1300                       1305

Pro Thr Pro Ala Val Val His Phe Lys Val Ser Ala Gln Gly Ile
    1310                         1315                       1320

Thr Leu Thr Asp Asn Gln Arg Lys Leu Phe Phe Arg Arg His Tyr
    1325                         1330                       1335

Pro Val Asn Ser Ile Thr Phe Ser Ser Thr Asp Pro Gln Asp Arg
    1340                         1345                       1350

Arg Trp Thr Asn Pro Asp Gly Thr Thr Ser Lys Ile Phe Gly Phe
    1355                         1360                       1365

Val Ala Lys Lys Pro Gly Ser Pro Trp Glu Asn Val Cys His Leu
    1370                         1375                       1380

Phe Ala Glu Leu Asp Pro Asp Gln Pro Ala Gly Ala Ile Val Thr
    1385                         1390                       1395

Phe Ile Thr Lys Val Leu Leu Gly Gln Arg Lys
    1400                         1405

<210> SEQ ID NO 2
<211> LENGTH: 24
<212> TYPE: DNA
<213> ORGANISM: Artificial Sequence
<220> FEATURE:
<223> OTHER INFORMATION: TENC1 forward primer

<400> SEQUENCE: 2
ctcagtggag tttgtttct cctc                                                          24

<210> SEQ ID NO 3
<211> LENGTH: 25
<212> TYPE: DNA
<213> ORGANISM: Artificial Sequence
<220> FEATURE:
<223> OTHER INFORMATION: TENC1 reverse primer

<400> SEQUENCE: 3
gctgattgaa gttttcatag gagtc                                                    25

<210> SEQ ID NO 4
<211> LENGTH: 25
<212> TYPE: DNA
<213> ORGANISM: Artificial Sequence
<220> FEATURE:
<223> OTHER INFORMATION: p85alpha forward primer

<400> SEQUENCE: 4
ggcgattaca ctcttacact aagga                                                    25

<210> SEQ ID NO 5
<211> LENGTH: 25
<212> TYPE: DNA
<213> ORGANISM: Artificial Sequence
<220> FEATURE:
<223> OTHER INFORMATION: p85alpha reverse primer -continued

```
<400> SEQUENCE: 5
gagttgaagg ttaatggatc agaga                                          25

<210> SEQ ID NO 6
<211> LENGTH: 24
<212> TYPE: DNA
<213> ORGANISM: Artificial Sequence
<220> FEATURE:
<223> OTHER INFORMATION: IRS-1 forward primer

<400> SEQUENCE: 6
gtgaacctca gtcccaacca taac                                           24

<210> SEQ ID NO 7
<211> LENGTH: 19
<212> TYPE: DNA
<213> ORGANISM: Artificial Sequence
<220> FEATURE:
<223> OTHER INFORMATION: IRS-1 reverse primer

<400> SEQUENCE: 7
ccggcaccct tgagtgtct                                                 19

<210> SEQ ID NO 8
<211> LENGTH: 21
<212> TYPE: DNA
<213> ORGANISM: Artificial Sequence
<220> FEATURE:
<223> OTHER INFORMATION: si6

<400> SEQUENCE: 8
tccgtggatt acaacacgac a                                              21

<210> SEQ ID NO 9
<211> LENGTH: 21
<212> TYPE: DNA
<213> ORGANISM: Artificial Sequence
<220> FEATURE:
<223> OTHER INFORMATION: si7

<400> SEQUENCE: 9
tccagtggac acagcacgct a                                              21
```